(12) United States Patent
Whitman (10) Patent No.: US 9,867,523 B2
(45) Date of Patent: *Jan. 16, 2018

(54) SURGICAL IMAGING DEVICE

(71) Applicant: COVIDIEN LP, Mansfield, MA (US)

(72) Inventor: Michael P. Whitman, New Hope, PA (US)

(73) Assignee: COVIDIEN LP, Mansfield, MA (US)

( * ) Notice: Subject to any disclaimer, the term of this patent is extended or adjusted under 35 U.S.C. 154(b) by 148 days.

This patent is subject to a terminal disclaimer.

(21) Appl. No.: 14/078,844

(22) Filed: Nov. 13, 2013

(65) Prior Publication Data

US 2014/0066702 A1 Mar. 6, 2014

Related U.S. Application Data

(60) Division of application No. 12/795,848, filed on Jun. 8, 2010, now Pat. No. 8,812,086, which is a
(Continued)

(51) Int. Cl.
*A61B 6/00* (2006.01)
*A61B 1/00* (2006.01)
(Continued)

(52) U.S. Cl.
CPC ...... *A61B 1/00147* (2013.01); *A61B 1/00009* (2013.01); *A61B 1/00016* (2013.01);
(Continued)

(58) Field of Classification Search
CPC .......... A61B 17/00234; A61B 19/5202; A61B 19/5212; A61B 19/5225; A61B 1/00009
See application file for complete search history.

(56) References Cited

U.S. PATENT DOCUMENTS 3,256,875 A 6/1966 Tsepelev et al.
3,858,577 A 1/1975 Bass et al.
(Continued)

FOREIGN PATENT DOCUMENTS

DE 42 13 426 10/1992
DE 196 26 433 1/1998
(Continued)

OTHER PUBLICATIONS

M. Kleinert, et al., "Special Pacemaker Catheter Techniques: The Transmediastinal Placement of Sensing Electrodes", *The Journal of Thoracic and Cardiovascular Surgery*; 1976.
(Continued)

*Primary Examiner* — Baisakhi Roy (57) ABSTRACT

A surgical imaging device and method configured to be inserted into a surgical site. The surgical imaging device includes a plurality of prongs. Each one of the prongs has an image sensor mounted thereon. The image sensors provide different image data corresponding to the surgical site, thus enabling a surgeon to view a surgical site from several different angles. The prongs may be moveable between a first position, suitable for insertion through a small surgical incision, and a second position, in which the prongs are separated from each other. In addition, the prongs may be bendable.

41 Claims, 9 Drawing Sheets

Related U.S. Application Data continuation of application No. 10/355,906, filed on Jan. 30, 2003, now Pat. No. 7,751,870.

(60) Provisional application No. 60/352,726, filed on Jan. 30, 2002.

(51) Int. Cl.

| | | |
|---|---|---|
| *A61B 1/313* | (2006.01) | |
| *A61B 17/00* | (2006.01) | |
| *A61B 1/04* | (2006.01) | |
| *A61B 1/06* | (2006.01) | |
| *A61B 1/07* | (2006.01) | |
| *A61B 90/30* | (2016.01) | |
| *A61B 90/00* | (2016.01) | |

(52) U.S. Cl.
CPC ...... *A61B 1/00018* (2013.01); *A61B 1/00025* (2013.01); *A61B 1/00045* (2013.01); *A61B 1/00114* (2013.01); *A61B 1/042* (2013.01); *A61B 1/0669* (2013.01); *A61B 1/07* (2013.01); *A61B 1/313* (2013.01); *A61B 1/3132* (2013.01); *A61B 17/00234* (2013.01); *A61B 90/30* (2016.02); *A61B 90/361* (2016.02); *A61B 90/37* (2016.02); *A61B 2017/003* (2013.01); *A61B 2090/3614* (2016.02)

(56) References Cited

U.S. PATENT DOCUMENTS

| | | | |
|---|---|---|---|
| 3,859,986 A | | 1/1975 | Okada et al. |
| 4,027,510 A | | 6/1977 | Hiltebrandt |
| 4,085,756 A | | 4/1978 | Weaver |
| 4,198,960 A | | 4/1980 | Utsugi |
| 4,250,873 A | | 2/1981 | Bonnet |
| 4,273,109 A | | 6/1981 | Enderby |
| 4,273,111 A | | 6/1981 | Tsukaya |
| 4,286,585 A | | 9/1981 | Ogawa |
| 4,367,729 A | | 1/1983 | Ogiu |
| 4,379,457 A | | 4/1983 | Gravener et al. |
| 4,402,311 A | | 9/1983 | Hattori |
| 4,448,188 A | | 5/1984 | Loeb |
| 4,494,549 A | | 1/1985 | Namba et al. |
| 4,499,895 A | | 2/1985 | Takayama |
| 4,559,928 A | | 12/1985 | Takayama |
| 4,593,679 A | | 6/1986 | Collins |
| 4,672,961 A | | 6/1987 | Davies |
| 4,674,515 A | | 6/1987 | Andou et al. |
| 4,732,156 A | | 3/1988 | Nakamura |
| 4,742,815 A | | 5/1988 | Ninan et al. |
| 4,756,309 A | | 7/1988 | Sachse et al. |
| 4,760,840 A | | 8/1988 | Fournier, Jr. et al. |
| 4,815,469 A | | 3/1989 | Cohen et al. |
| 4,819,632 A | | 4/1989 | Davies |
| 4,880,015 A | | 11/1989 | Nierman |
| 4,890,602 A | | 1/1990 | Hake |
| 4,893,613 A | | 1/1990 | Hake |
| 4,907,588 A | | 3/1990 | Burston |
| 4,907,973 A | | 3/1990 | Hon |
| 4,928,699 A | | 5/1990 | Sasai |
| 4,930,494 A | | 6/1990 | Takehana et al. |
| 4,941,454 A | | 7/1990 | Wood et al. |
| 4,944,443 A | | 7/1990 | Oddsen et al. |
| 4,955,882 A | | 9/1990 | Hakky |
| 4,976,710 A | | 12/1990 | Mackin |
| 4,982,726 A | | 1/1991 | Taira |
| 4,994,060 A | | 2/1991 | Rink et al. |
| 5,133,713 A | | 7/1992 | Huang et al. |
| 5,134,281 A | | 7/1992 | Bryenton et al. |
| 5,186,714 A | | 2/1993 | Boudreault et al. |
| 5,197,649 A | | 3/1993 | Bessler et al. |
| 5,201,325 A | | 4/1993 | McEwen et al. |
| 5,201,730 A | | 4/1993 | Easley et al. |
| 5,207,697 A | | 5/1993 | Carusillo et al. |
| 5,217,003 A | | 6/1993 | Wilk |
| 5,221,959 A | * | 6/1993 | Ohyama et al. ............... 356/326 |
| 5,243,967 A | | 9/1993 | Hibino |
| 5,251,613 A | | 10/1993 | Adair |
| 5,258,008 A | | 11/1993 | Wilk |
| 5,305,121 A | | 4/1994 | Moll |
| 5,306,234 A | | 4/1994 | Johnson |
| 5,322,055 A | | 6/1994 | Davison et al. |
| 5,330,486 A | | 7/1994 | Wilk |
| 5,333,772 A | | 8/1994 | Rothfuss et al. |
| 5,333,773 A | | 8/1994 | Main et al. |
| 5,354,266 A | | 10/1994 | Snoke |
| 5,368,015 A | * | 11/1994 | Wilk ............................ 600/104 |
| 5,383,880 A | | 1/1995 | Hooven |
| 5,395,030 A | | 3/1995 | Kuramoto et al. |
| 5,411,508 A | | 5/1995 | Bessler et al. |
| 5,437,636 A | | 8/1995 | Snoke et al. |
| 5,441,507 A | | 8/1995 | Wilk |
| 5,460,182 A | | 10/1995 | Goodman et al. |
| 5,496,269 A | | 3/1996 | Snoke |
| 5,531,687 A | | 7/1996 | Snoke et al. |
| 5,540,711 A | | 7/1996 | Kieturakis et al. |
| 5,603,688 A | | 2/1997 | Upsher |
| 5,604,531 A | | 2/1997 | Iddan et al. |
| 5,609,560 A | | 3/1997 | Ichikawa et al. |
| 5,630,782 A | | 5/1997 | Adair |
| 5,645,519 A | * | 7/1997 | Lee ........................ A61B 1/303 |
| | | | 600/114 |
| 5,653,677 A | | 8/1997 | Okada et al. |
| 5,662,680 A | | 9/1997 | Desai |
| 5,667,473 A | | 9/1997 | Finn et al. |
| 5,667,478 A | | 9/1997 | McFarcin et al. |
| 5,667,517 A | | 9/1997 | Hooven |
| 5,797,835 A | | 8/1998 | Green |
| 5,797,944 A | | 8/1998 | Nobles et al. |
| 5,815,640 A | | 9/1998 | Wang et al. |
| 5,855,583 A | | 1/1999 | Wang et al. |
| 5,857,996 A | | 1/1999 | Snoke |
| 5,865,728 A | | 2/1999 | Moll et al. |
| 5,868,760 A | | 2/1999 | McGuckin, Jr. |
| 5,878,193 A | | 3/1999 | Wang et al. |
| 5,882,331 A | | 3/1999 | Sasaki |
| 5,907,664 A | | 5/1999 | Wang et al. |
| 5,910,152 A | | 6/1999 | Bays |
| 5,920,390 A | | 7/1999 | Farahi et al. |
| 5,935,143 A | | 8/1999 | Hood |
| 5,941,818 A | | 8/1999 | Hori et al. |
| 5,954,634 A | | 9/1999 | Igarashi |
| 5,954,642 A | | 9/1999 | Johnson et al. |
| 5,968,060 A | | 10/1999 | Kellogg |
| 5,989,184 A | | 11/1999 | Blair |
| 5,989,274 A | | 11/1999 | Davison et al. |
| 5,993,378 A | | 11/1999 | Lemelson |
| 5,995,645 A | | 11/1999 | Soenksen et al. |
| 6,015,969 A | | 1/2000 | Nathel et al. |
| 6,019,719 A | | 2/2000 | Schulz et al. |
| 6,027,515 A | | 2/2000 | Cimino |
| 6,056,735 A | | 5/2000 | Okada et al. |
| 6,063,095 A | | 5/2000 | Wang et al. |
| 6,066,090 A | | 5/2000 | Yoon |
| 6,068,627 A | | 5/2000 | Orszulak et al. |
| 6,068,647 A | | 5/2000 | Witt et al. |
| 6,069,689 A | | 5/2000 | Zeng et al. |
| 6,074,402 A | | 6/2000 | Peifer et al. |
| 6,077,285 A | | 6/2000 | Boukhny |
| 6,083,191 A | | 7/2000 | Rose |
| 6,086,528 A | * | 7/2000 | Adair ............................ 600/104 |
| 6,099,466 A | | 8/2000 | Sano et al. |
| 6,099,537 A | | 8/2000 | Sugai et al. |
| 6,117,152 A | | 9/2000 | Huitema |
| 6,124,597 A | | 9/2000 | Shehada et al. |
| 6,126,591 A | | 10/2000 | McGarry et al. |
| 6,134,003 A | | 10/2000 | Tearney et al. |
| 6,139,561 A | | 10/2000 | Shibata et al. |
| 6,142,930 A | | 11/2000 | Ito et al. |
| 6,159,225 A | | 12/2000 | Makower |
| 6,163,378 A | | 12/2000 | Khoury |
| 6,208,749 B1 | | 3/2001 | Gutkowicz-Krusin et al. |

(56) References Cited

U.S. PATENT DOCUMENTS

| | | | |
|---|---|---|---|
| 6,208,887 B1 | 3/2001 | Clarke | |
| 6,211,904 B1 | 4/2001 | Adair et al. | |
| 6,215,550 B1 | 4/2001 | Baer et al. | |
| 6,224,227 B1 | 5/2001 | Klootz | |
| 6,236,502 B1 | 5/2001 | Kitajima | |
| 6,238,386 B1 | 5/2001 | Miller et al. | |
| 6,240,305 B1 | 5/2001 | Tsuchiya | |
| 6,244,809 B1 | 6/2001 | Wang et al. | |
| 6,245,058 B1 | 6/2001 | Suzuki | |
| 6,251,101 B1 | 6/2001 | Glockler | |
| 6,263,227 B1 | 7/2001 | Boggett et al. | |
| 6,309,375 B1* | 10/2001 | Glines et al. | 604/187 |
| 6,319,199 B1 | 11/2001 | Sheehan et al. | |
| 6,331,181 B1 | 12/2001 | Tierney et al. | |
| 6,364,888 B1 | 4/2002 | Niemeyer et al. | |
| 6,398,726 B1 | 6/2002 | Ramans et al. | |
| 6,412,980 B1* | 7/2002 | Lounsberry et al. | 378/207 |
| 6,447,444 B1 | 9/2002 | Avni et al. | |
| 6,485,413 B1* | 11/2002 | Boppart et al. | 600/160 |
| 6,535,764 B2 | 3/2003 | Imran et al. | |
| 6,556,858 B1* | 4/2003 | Zeman | 600/473 |
| 6,750,971 B2 | 6/2004 | Overbeck et al. | |
| 6,775,565 B1* | 8/2004 | Wieringa | 600/322 |
| 6,929,600 B2 | 8/2005 | Hill | |
| 7,052,492 B2* | 5/2006 | Swanson et al. | 606/32 |
| 7,282,034 B2* | 10/2007 | Burbank et al. | 600/564 |
| 7,751,870 B2* | 7/2010 | Whitman | 600/476 |
| 2001/0000672 A1 | 5/2001 | Yamakita et al. | |
| 2001/0001812 A1 | 5/2001 | Valley et al. | |
| 2001/0016725 A1 | 8/2001 | Valley et al. | |
| 2002/0159529 A1 | 10/2001 | Wang et al. | |
| 2002/0026094 A1 | 2/2002 | Roth | |
| 2002/0032451 A1 | 3/2002 | Tierney et al. | |
| 2002/0032452 A1 | 3/2002 | Tierney et al. | |
| 2002/0042620 A1 | 4/2002 | Julian et al. | |
| 2002/0049454 A1 | 4/2002 | Whitman et al. | |
| 2002/0055795 A1 | 5/2002 | Niemeyer et al. | |
| 2002/0072739 A1* | 6/2002 | Lee et al. | 606/41 |
| 2002/0092533 A1 | 7/2002 | Boyd et al. | |
| 2002/0165444 A1 | 11/2002 | Whitman | |
| 2002/0183758 A1* | 12/2002 | Middleton | A61B 17/1617 606/79 |
| 2003/0078476 A1 | 4/2003 | Hill | |
| 2003/0109870 A1 | 6/2003 | Lee et al. | |
| 2004/0030382 A1 | 2/2004 | St. Goar et al. | |
| 2004/0039442 A1 | 2/2004 | St. Goar et al. | |
| 2005/0216019 A1* | 9/2005 | Eckman | 606/79 |

FOREIGN PATENT DOCUMENTS

| | | |
|---|---|---|
| EP | 0 305 170 | 3/1989 |
| EP | 0 341 719 | 5/1989 |
| EP | 0 667 115 | 8/1995 |
| EP | 0 774 231 | 5/1997 |
| EP | 0 653 922 | 12/1999 |
| GB | 2 128 881 | 5/1984 |
| GB | 2 291 980 | 2/1996 |
| JP | 59 223079 | 12/1984 |
| JP | 2003080212 | 4/1991 |
| WO | WO 82/03545 | 10/1982 |
| WO | WO 83/00992 | 3/1983 |
| WO | WO 92/16141 | 10/1992 |
| WO | WO 98/32380 | 7/1998 |
| WO | WO 99/30610 | 6/1999 |
| WO | WO 99/32028 | 7/1999 |
| WO | WO 00/22975 | 4/2000 |
| WO | WO 00/76391 | 12/2000 |
| WO | WO 01/03587 | 1/2001 |
| WO | WO 01/08572 | 2/2001 |
| WO | WO 01/10291 | 2/2001 |
| WO | WO 01/35813 | 5/2001 |
| WO | WO 01/62163 | 8/2001 |
| WO | WO 02/55126 | 7/2002 |

OTHER PUBLICATIONS

T. Tanabe, et al., "Cardiovascular Fiberoptic Endoscopy: Development and Clinical Application", *Surgery*, vol. 87, No. 4; Apr. 1980.

E. D. Mayer, et al., "Case Report—Late Pulmonary Embolization of a Retained Pacemaker Electrode Fragment After Attempted Transatrial Extraction"; *The Thoracic and Cardiovascular Surgeon* 33; 1985.

P. Raj Behl, et al., "Technical Note—Mediastinoscope: Another Use", *The Journal of Cardiovascular Surgery*, vol. 27, No. 2; Mar.-Apr. 1986.

R. J. Pierce, et al., "Endobronchial Resection with the Nd-YAG Laser—Two Years Experience in an Australian Unit", *Australia/New Zealand Journal of Medicine*, vol. 20, No. 2; Apr. 1990.

Alan R. Hartman, et al., "Fiberoptic Examination of the Inferior Vena Cava During Circulatory Arrest for Complete Removal of Renal Cell Carcinoma Thrombus", *Surgery*, vol. 107, No. 6; Jun. 1990.

Mitchell S. Cappell, "Case Report—Manometric Findings in Dysphagia Secondary to Left Atrial Dilation—Giant, Cyclic Midesophageal Pressure Waves Occurring with Every Heart Beat", *Digestive Diseases and Sciences*, vol. 36, No. 5; May 1991.

Stephen D. Hill, "An Apparatus and Method for Intubation", U.S. Appl. No. 60/307,134, filed Jul. 24, 2001; 13 Pages.

New York Magazine, The Best Doctors in New York, p. 80; Jun. 10, 2002.

* cited by examiner

SURGICAL IMAGING DEVICE

CROSS-REFERENCE TO RELATED APPLICATIONS

The present application is a Divisional Application which claims the benefit of and priority to U.S. patent application Ser. No. 12/795,848, filed on Jun. 8, 2010, which is a Continuation of U.S. patent application Ser. No. 10/355,906, filed on Jan. 30, 2003, now U.S. Pat. No. 7,751,870, which claims the benefit of and priority under 35 U.S.C. §119(e) of U.S. Provisional Patent Application No. 60/352,726, filed on Jan. 30, 2002, the entire content of each of which being incorporated herein by reference.

FIELD OF THE INVENTION

The present invention relates to a surgical imaging device, and in particular to a surgical imaging device that is configured to provide image data of a body cavity.

BACKGROUND INFORMATION

It is typically important during a surgical procedure that a surgeon be able to view the surgical site so as to ensure that the surgical procedure is being performed correctly. However, there are many types of surgical procedures in which the surgeon is not able to see the surgical site. For instance, laparoscopic or endoscopic surgical procedures, in which a surgeon accesses a surgical site through very small incisions, prevent the surgeon from viewing the surgical site.

One method for performing surgical procedures of this type is to employ surgical devices that include arrangements for indicating the position of components of the surgical devices while in use. For instance, a surgical device for such a surgical procedure may include a remote status indicator that provides an indication of the position of a component of the surgical device, such as the position of a clamp or staple cartridge. By knowing the position of the components of the surgical device, the surgeon may determine if the surgical device is being operated correctly during the surgical procedure.

Another method for performing surgical procedures of this type is to employ a video camera or the like. For instance, various types of cameras may be configured to be inserted through an incision in a patient and into a surgical site. Such cameras provide video data of the surgical site during a surgical procedure, thereby allowing the surgeon to see the surgical procedure taking place in real time. However, once one of these cameras is inserted through an incision and into a surgical site, it may be difficult to maneuver due to the fact that it is prevented from movement in most directions by the small incision. In addition, these cameras provide only a single view of the surgical site. If the surgeon needs to change the view of the surgical site, e.g., to examine the surgical site from a different angle, the surgeon typically is required to remove the camera from the first incision, to make another incision in the patient, and to reinsert the camera into the second incision.

SUMMARY

In accordance with one example embodiment of the present invention, a surgical imaging device is provided. The surgical imaging device is configured to be inserted into a surgical site. The surgical imaging device includes a plurality of prongs. Each one of the prongs has an image sensor mounted thereon. The image sensors provide different image data corresponding to the surgical site, thus enabling a surgeon to view a surgical site from several different angles.

The prongs may be moveable between a first position, in which the prongs are substantially parallel to each other, and a second position, in which the prongs are not substantially parallel to each other. In the substantially parallel configuration, e.g., the first position, the prongs are configured to be inserted through an incision into the surgical site. Once inserted through the incision into the surgical site, the prongs may be radially separated from each other by a user rotating control levers that are connected to the prongs by legs.

In addition, the prongs may be bendable between an extended position, in which the prongs are substantially perpendicular to their respective legs, and a retracted position, in which the prongs are not substantially perpendicular to their respective legs. Advantageously, the prongs are configured to bend in conformance with a shape of a cavity that is formed in the surgical site by the actuation of an actuator configured to form such a cavity.

The surgical imaging device may be configured for operation in a wired format, a wireless format, or both. In the wired format, the device may include a body portion having a slot in electrical communication with the image sensors, a video display device configured to display the image data, and a control cable that is configured to the transmit image data from the image sensor to the video display device. In the wired format, the device may also include a power supply coupleable to the control cable for supplying power to the device. In the wireless format, the device may include a body portion having a first antenna and a remote control device having a second antenna, wherein the remote control device is configured to provide a wireless control signal via the second antenna to the device via the first antenna. In addition, in the wireless format, the device may include a video display device having an antenna, wherein the device is configured to generate via the first antenna a wireless signal corresponding to image data from the image sensors, and wherein the video display device is configured to receive the wireless signal and to provide a display corresponding to the image data. In the wireless format, the device may also include a local power supply for providing power to the device.

BRIEF DESCRIPTION OF THE DRAWINGS

FIGS. 11(*a*) to 11(*c*) illustrate the operation of the surgical imaging device to perform an exemplary type of surgical procedure, according to one example embodiment of the present invention.

DETAILED DESCRIPTION

Figure 1:
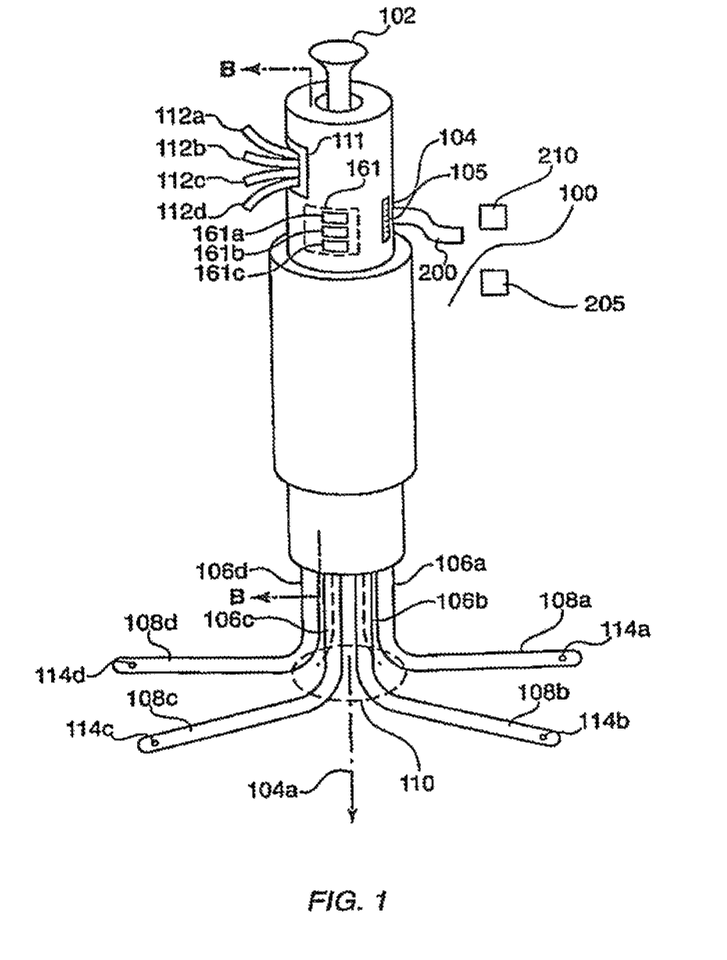
FIG. 1 shows a perspective view of a surgical imaging device, in accordance with one embodiment of the present invention.

FIG. 1 shows a perspective view of a surgical imaging device 100 according to an example embodiment of the present invention. The surgical imaging device 100 includes a body portion 104 which encloses legs 106*a* to 106*d* and a retraction actuator 102. The legs 106*a* to 106*d* are connected to levers 112*a* to 112*d*, respectively. Prongs 108*a* to 108*d* extend from legs 106*a* to 106*d*, respectively. Located at or near the distal tip of each prong 108*a* to 108*d* is a camera 114*a* to 114*d*, respectively.

According to one embodiment of the present invention, the legs 106*a* to 106*d*, along with their respective prongs 108*a* to 108*d*, are moveable. For instance, the legs 106*a* to 106*d* may be moveable within a cylindrical opening of the body portion 104 (explained in more detail below) so that the legs 106*a* to 106*d* move radially around a central axis 104*a* of the body portion 104. In addition, the legs 106*a* to 106*d* may be rotatably moveable, e.g., rotatable around their own central axes, within the body portion 104, so that the prongs 108*a* to 108*d* may be caused to swivel around the central axes of the legs 106*a* to 106*d*, respectively. The legs 106*a* to 106*d* may be moveable in both of these ways by the operation of the levers 112*a* to 112*d*, respectively, as further described below. The control levers 112*a* to 112*d* extend through opening 111. Specifically, the movement of the legs 106*a* to 106*d* within the body portion 104 is more fully described below in connection with FIGS. 6, 7 and 8.

In addition, the prongs 108*a* to 108*d* may be moveable relative to their respective legs 106*a* to 106*d*. For instance, the prongs 108*a* to 108*d* may be moveable between an extended position, in which each prong 108*a* to 108*d* is positioned in substantially the same plane, e.g., each being substantially perpendicular to its respective legs 106*a* to 106*d*, and a retracted position, in which each prong 108*a* to 108*d* is not positioned in substantially the same plane, e.g., is not substantially perpendicular to its respective legs 106*a* to 106*d*. The movement of the prongs 108*a* to 108*d* between an extended position and a retracted position is more fully described below in connection with FIG. 9.

The body portion 104 may also include a memory device 161. In one embodiment of the present invention, the memory device 161 stores data corresponding to the surgical imaging device 100. For instance, the memory device 161 may store data corresponding to an operating program which controls the operation of the surgical imaging device 100. For instance, the operating program may include data that controls or operates the various functions of the surgical imaging device 100, such as lens movement, adjustment of light intensity, zoom magnification, color, brightness and focus.

Data stored in the memory device 161 may include model/serial number identification 161*a*, usage data 161*b* and image data 161*c*. The model/serial number identification 161*a* uniquely identifies the surgical imaging device 100. The usage data 161*b* may include, e.g., information concerning the number of hours the surgical imaging device 100 has been used and the types of procedures that have been viewed using the surgical imaging device 100. The image data 161*c* may include, e.g., video clips, still frames, etc., which depict visual images of the body cavity. In one embodiment of the present invention, the user may label and categorize the image data 161*c* while using the imaging device 100 during a surgical procedure. In addition, the usage data 161*b* and image data 161*c* may be transferred for permanent storage on a storage device, e.g., floppy disk, CD, hard drive disk, etc., so that a surgeon may review the stored data at a future date.

The body portion 104 of the surgical imaging device 100 may also include a slot 105 configured to receive a control cable 200, as further described below in connection with FIG. 5. Generally, the control cable 200 conveys data and/or power between the cameras 114*a* to 114*d* and a video display device 205 and/or a power supply 210.

Figure 2:
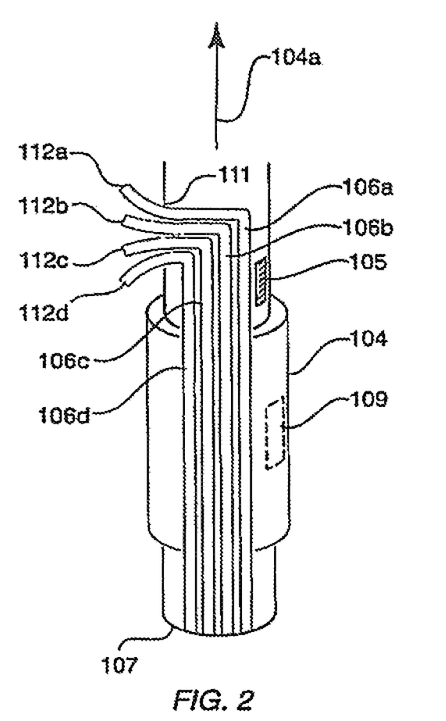
FIG. 2 illustrates a cross-sectional view of a body portion of the surgical imaging device shown in FIG. 1, taken along the lines B-B.

FIG. 2 illustrates a cross-sectional view of the body portion 104 shown in FIG. 1, taken along the lines B-B. As previously mentioned, in this embodiment, the legs 106*a* to 106*d* connect to control levers 112*a* to 112*d*, respectively. The control levers 112*a* to 112*d* extend through opening 111 and may be movable in a radial direction relative to the central axis 104*a* of the body portion 104. The legs 106*a* to 106*d* extend axially through the body portion 104 and out of cylindrical opening 107. The opening 111 is configured so as to provide sufficient movement to the control levers 112*a* to 112*d* to enable the legs 106*a* to 106*d* to be moved between different positions in the cylindrical opening 107 of the body portion 107, as further described below.

Figure 3:
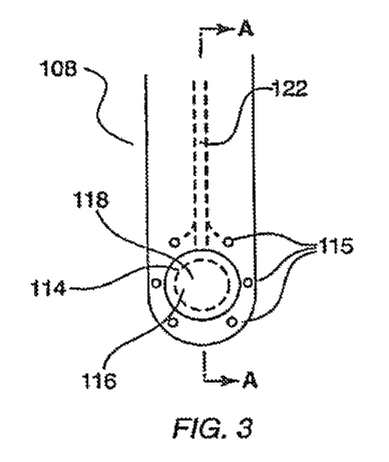
FIG. 3 illustrates a prong having a camera, according to one embodiment of the present invention.
Figure 4:
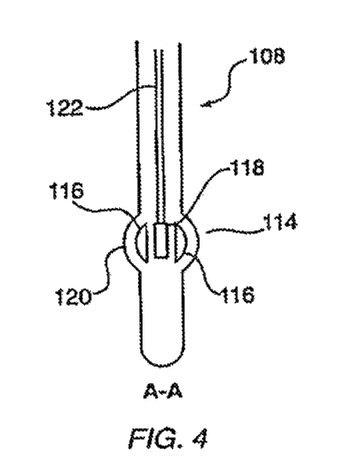
FIG. 4 is a cross-sectional view of the prong shown in FIG. 3, taken along the lines A-A.

As described above, located at or near the distal tip of prongs 108*a* to 108*d* are cameras 114*a* to 114*d*, respectively. FIGS. 3 and 4 illustrate a prong 108 having a camera 114, according to one embodiment of the present invention. In FIG. 3 there is shown a camera 114 that includes a lens 116 and an imaging sensor 118. One or more light sources 115 may be mounted adjacent to the camera 114 and provide light to enable the imaging sensor 118 to sense an image. The prong 108 may also include a control line 122 having control and power leads that transmit power to the imaging sensor 118 and to the light sources 155, and/or transmit image data signals to and from the imaging sensor 118. The light sources 115 may include, e.g., light-emitting diodes.

FIG. 4 is a cross-sectional view of the prong 108 shown in FIG. 3, taken along the lines A-A. FIG. 4 illustrates the camera 114 including a pair of lenses 116, lens covers 120 for protecting the lenses 116, and the imaging sensor 118. The imaging sensor 118 may be, for example, a charged coupled device (hereinafter referred to as a "CCD"). The imaging sensor 118 receives an image from lens 116 and converts the image to image data, e.g., electronic signals, for transmission through the control line 122. The camera 114 may also include internal circuitry that converts images captured by the imaging sensor 118 into electrical signals for transmission to a video display device.

Although one embodiment of the present invention employs a CCD as the imaging sensor 118, other suitable imaging sensors may also be used. In another exemplary embodiment of the present invention, the imaging sensor 118 is an integrated circuit using a Complementary Metal Oxide Semiconductor (hereinafter referred to as "CMOS")

process. A CMOS type image sensor may include a photo diode or photo transistor as the light detecting element. Furthermore, a CMOS image sensor may transmit analog signals or use an analog-digital converter for signal transmission. The CMOS sensor may provide an alternative to the CCD sensor that would require less power during operation due to its greater sensitivity to light. U.S. patent application Ser. No. 10/127,310, filed on Apr. 27, 2002, which is expressly incorporated herein by reference in its entirety, describes other possible imaging devices and arrangements that may be used in connection with the example embodiment.

Figure 5:
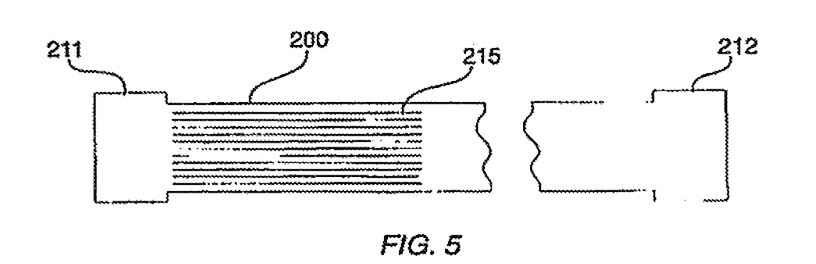
FIG. 5 illustrates a control cable, according to one embodiment of the present invention.

FIG. 5 illustrates a control cable 200 according to one embodiment of the present invention. The control cable 200 includes coupling 211, leads 215 and coupling 212. The control cable 200 is configured to attach, via coupling 211, to slot 105 located on body portion 104. Leads 215 transmit signals to and from the imaging sensors 118 in each cameras 114a to 114d. In addition, leads 215 may transmit power for energizing the various components of the cameras 114a to 114d. The coupling 212 is configured to attach to the video display device 205, such as a television monitor, computer monitor, CRT or similar viewing device, which receives and processes the image data for viewing, and/or to attach to a power supply 205.

Figure 6:
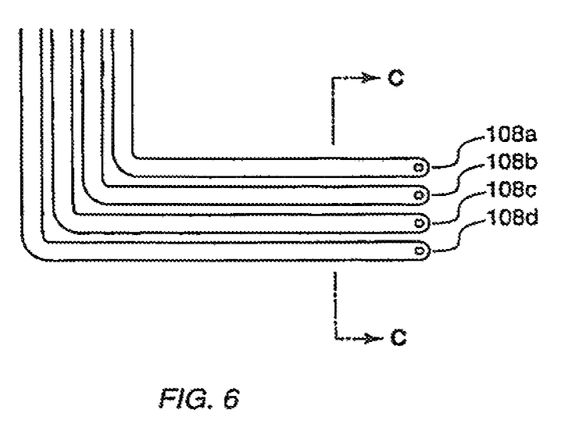
FIG. 6 illustrates the legs and prongs of the surgical imaging device in a first position, according to one embodiment of the present invention.
Figure 7:
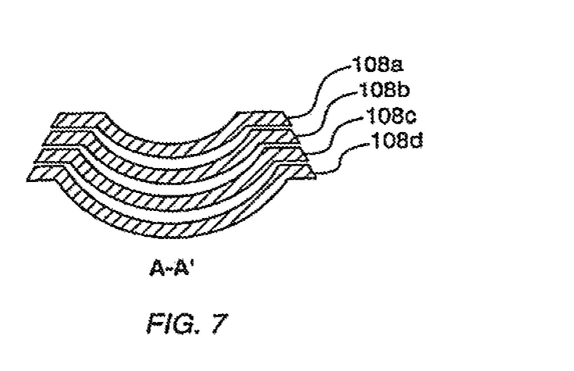
FIG. 7 illustrates a cross-sectional view of the prongs shown in FIG. 6, taken along the lines C-C.

As described above, in one embodiment of the present invention, the legs 106a to 106d, along with their respective prongs 108a to 108d, are moveable between various positions. For instance, the legs 106a to 106d, along with their respective prongs 108a to 108d, may be moveable between a first position, in which the prongs 108a to 108d are parallel to each other, and a second position, in which the distal ends of the prongs 108a to 108d are not parallel to each other. FIG. 6 illustrates the legs 106a to 106d, along with their respective prongs 108a to 108d, in a first position. In this first position, the legs 106a to 106d are rotated in the body portion 104 such that the distal ends of the prongs 108a to 108d, e.g., the ends of the prongs 108a to 108d having the cameras 114a to 114d, respectively, are positioned adjacent to each other. In one embodiment of the present invention, the prongs 108a to 108d are configured so as to fit together, thereby reducing the cross-sectional area of the distal ends of the prongs 108a to 108d. For instance, FIG. 7 illustrates a cross-sectional view of the prongs 108a to 108d shown in FIG. 6, taken along the lines C-C, wherein the distal ends of the prongs 108a to 108d each have a complementary cross-sectional shape relative to each other so as to minimize the cross-sectional areas of the prongs 108a to 108d when parallel to each other. This parallel position is suitable for maneuvering the prongs 108a to 108d into and out of an incision in a patient, as more fully described below.

FIG. 1, explained in detail above, illustrates the legs 106a to 106d, along with their respective prongs 108a to 108d, in the second position. In this second position, the legs 106a to 106d are rotated in the body portion 104 such that the prongs 108a to 108d are moved within a substantially same plane, e.g., a plane that is substantially perpendicular to the central axis 104a of the body portion 104, so as to be not parallel to each other. For instance, FIG. 1 illustrates the legs 106a to 106d, along with their respective prongs 108a to 108d, rotated in the body portion 104 such that the prongs 108a to 108d are radially separated relative to each other and positioned approximately 90 degrees apart from each other relative to the central axis 104a of the body portion 104.

Figure 8:
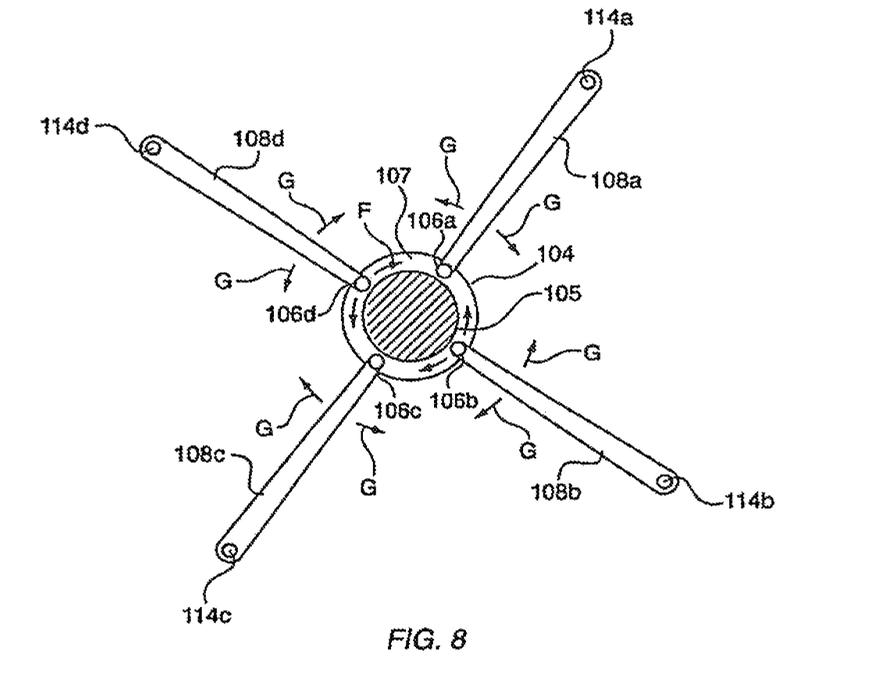
FIG. 8 is a bottom view of the surgical imaging device shown in FIG. 1.

Another view of the legs 106a to 106d and the prongs 108a to 108d in the second position is shown in FIG. 8. FIG. 8 is a bottom view of the surgical imaging device 100 shown in FIG. 1. In the embodiment shown in FIG. 8, arrows F illustrate the directions that the legs 106b, 106c and 106d may move within the cylindrical opening 107 of the body portion 104. In addition, arrows G illustrate the directions that the prongs 108a to 108d may move when their respective legs 106a to 106d are rotated around their respective central axes.

Figure 9:
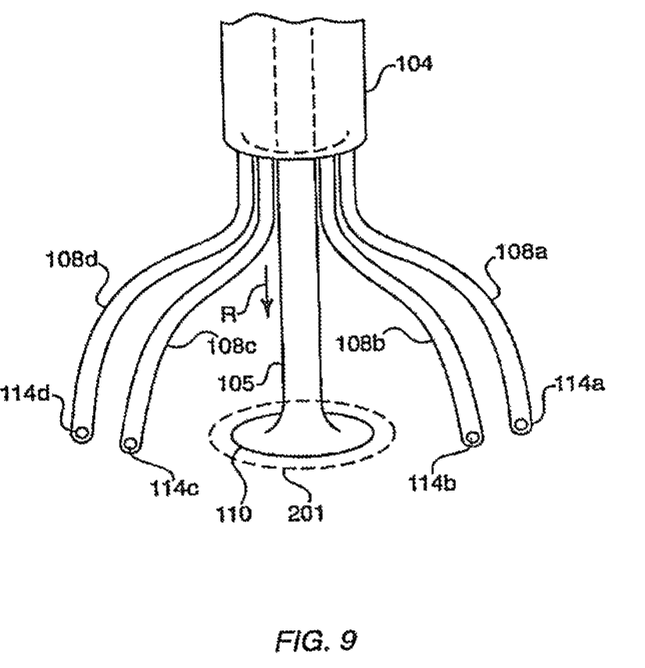
FIG. 9 illustrates the surgical imaging device shown in FIG. 1 in a retracted position, according to one embodiment of the present invention.

As previously mentioned, in addition to the movement of the legs 106a to 106d and their prongs 108a to 108d as shown in FIG. 8, the prongs 108a to 108d are also moveable between an extended position and a retracted position. FIG. 1, described above, illustrates the prongs 108a to 108d in an extended position, in which each prong 108a to 108d is in a substantially same plane, e.g., each being substantially perpendicular to its respective legs 106a to 106d. FIG. 9, on the other hand, illustrates the surgical imaging device 100 in a retracted position. As mentioned previously, in the embodiment shown, the prongs 108a and 108b of the surgical imaging device 100 are not substantially perpendicular to their respective legs 106a to 106d in the retracted position. In the retracted position, the prongs 108a to 108d of the surgical imaging device 100 are moved relative to their respective legs 106a to 106d such that the camera 114a to 114d of each of the prongs 108a to 108b is directed to a region of space. In one embodiment of the present invention, the prongs 108a to 108d of the surgical imaging device 100 are moved relative to their respective legs 106a to 106d such that the imaging sensor 118 mounted in each of the prongs 108a to 108b is directed to the same region of space, such as region of space 201 illustrated in FIG. 9. The region of space 201 may be a region of space in which a surgical instrument is being used during a surgical procedure. Thus, in this embodiment, in the retracted position, the imaging sensor 118 of each of the prongs 108a to 108b provide a view of a surgical site during a surgical procedure from a different angle. Alternatively, the prongs 108a to 108d of the surgical imaging device 100 may be moved such that the imaging sensor 118 of each of the prongs 108a to 108b are directed to different regions of space.

In one embodiment, the surgical imaging device 100 is moved from an extended position into the retracted position by the actuation of the retraction actuator 105. The retraction actuator 105 moves axially relative to the body portion 104 such that, during retraction, the bottom portion 110 of the retraction actuator 102 moves away from the body portion 104 in the direction indicated by arrow R. The prongs 108a to 108d are preferably made of a flexible material, enabling the prongs 108a to 108d to bend when force is exerted thereon. For instance, as the bottom portion of the retraction actuator 102 is moved into a body cavity, a force may be exerted on the prongs 108a to 108d by the walls of a body cavity. As a result, the prongs 108a to 108d may be caused to bend and may form, as shown in FIG. 9, a curved shape. In one embodiment, the curved shape of each of the prongs 108a to 108d conform to the walls of the body cavity in which the prongs 108a to 108d are disposed. In this manner, the imaging sensor 118 positioned at the tip of each prong 108a to 108d may provide a user with multiple views of the body cavity area. In addition, the user may rotate each prong 108a to 108d in order to view the body cavity from various angles.

Figure 10:
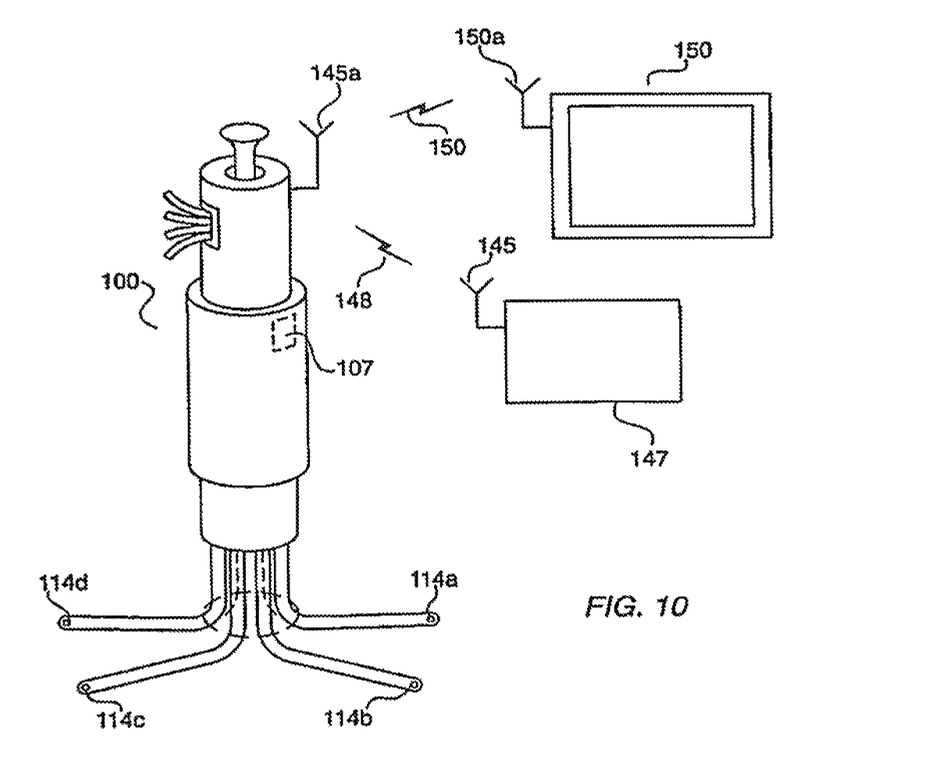
FIG. 10 illustrates a wireless arrangement for wirelessly transmitting image data for display on a video display device, according to one embodiment of the present invention.

As previously described, the image data may be transmitted via the control cable 200 inserted at one end into the slot 105 of the body portion 104 and inserted at the other end to a video display device 205. Alternatively, the image data may be transmitted wirelessly for display on a video display device. For instance, the surgical imaging device 100 may include a wireless arrangement for wirelessly transmitting the image data for display on a video display device. FIG. 10 illustrates one embodiment of the present invention that employs a wireless arrangement for wirelessly transmitting the image data for display on a video display device. Specifically, and as illustrated in FIG. 10, the surgical imaging device 100 may include an antenna 145a configured to transmit image data and/or control signals. The antenna 145a of the surgical imaging device 100 may receive control signals 148 from the antenna 145b of a remote control unit 147. These control signals may include, for instance, signals that control the imaging sensors 118, the intensity of the light provided by the light sources 115, or any other signals for controlling the operation of the surgical imaging device 100. In addition, the surgical imaging device 100 may transmits video signals 158 via the antenna 145a of the surgical imaging device 100 to an antenna 150a of a video display device 150.

In another embodiment, the cameras 114a to 114d may include wireless circuitry that enables the transmission of wireless signals 158 directly to the video display device 150. Since the wireless embodiment of the surgical imaging device 100 enables the control cable 200 and the power supply 210 to be eliminated, the surgical imaging device 100 may, as shown in FIG. 10, include a local power source, e.g., a battery, 109. The local power source 109 may supply power to the imaging sensors 118, the light sources 115, any additional internal circuitry in the cameras 114a to 114d, etc. In this wireless embodiment of the present invention, the surgical imaging device 100 may also eliminate the slot 105 of the body portion 104 (shown in FIG. 1) that is configured to receive the control cable 200.

In still another embodiment, the surgical imaging device 100 may be equipped to alternatively function in either a wired or wireless format. In this embodiment, the slot 105 may have a cover which would enable the user to cover the slot 105 when the imaging device 100 is operated wirelessly. Should the user desire to operate the surgical imaging device 100 in a wired format, the user may remove the cover and attach the control cable 200 into the slot 105. In this embodiment, the operating program for the imaging device 100 is advantageously configured to detect when the control cable 200 is or is not attached to the slot, and to operate the surgical imaging device 100 in either the wired or the wireless formats in accordance therewith.

Figure 12:
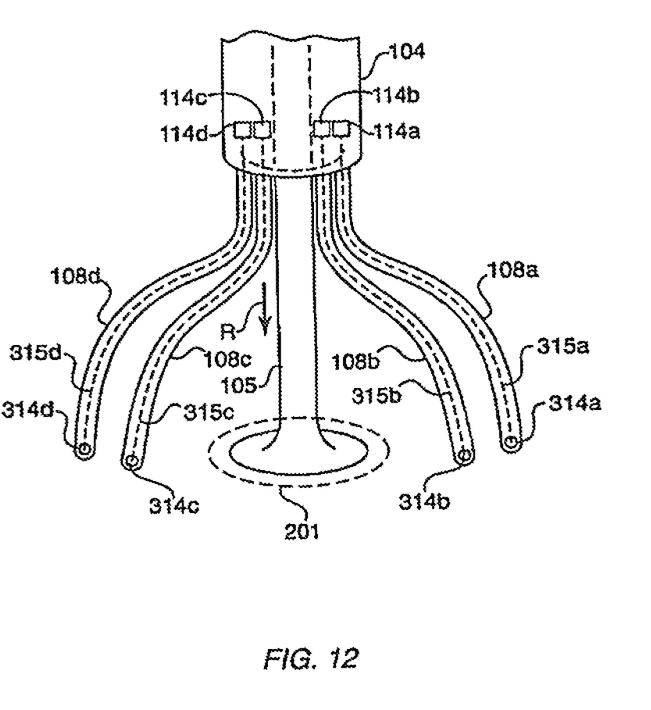
FIG. 12 illustrates a surgical imaging device having imaging sensors provided in a body portion, according to one example embodiment of the present invention.

In another example embodiment of the present invention, one or more imaging sensors, e.g., imaging sensors 118, may be provided in the body portion, e.g., body portion 104, or in a remote device. FIG. 12 illustrates one example embodiment having imaging sensors 118 provided in the body portion 104. In this embodiment, the prongs 108a to 108d include light guides, such as light guides 315a to 315d, and/or a lens system, such as lens systems 314a to 314d, which guide light reflected in the body cavity to the imaging sensors 118a to 118d in order to remotely capture an image of the body cavity. For example, fiber optics may be used in this regard.

Figure 11A:
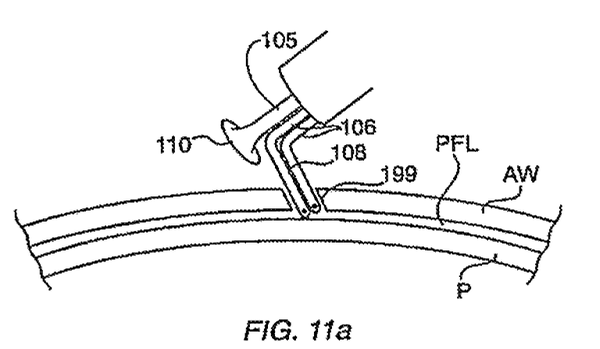
Figure 11B:
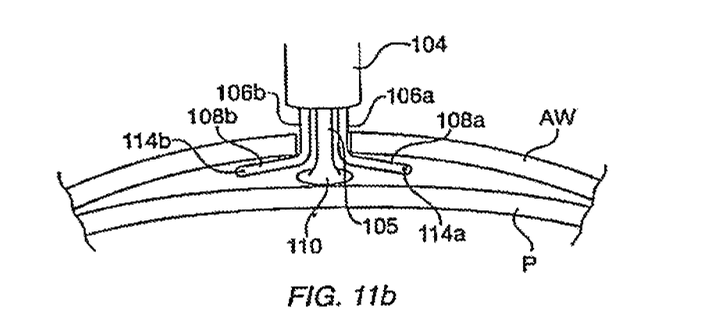
Figure 11C:
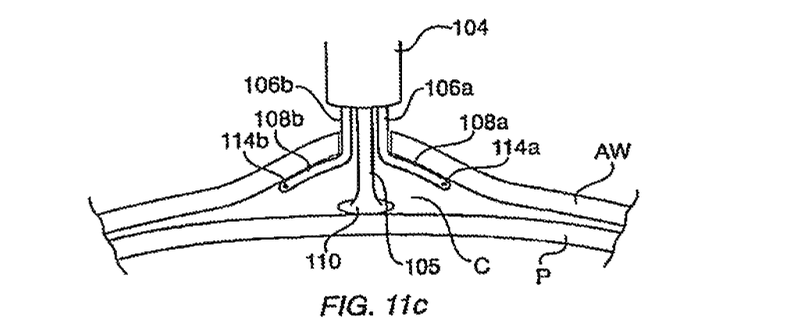

The surgical imaging device 100 of the present invention may be used in various types of surgical procedures. FIGS. 11(a) to 11(c) illustrate the operation of the surgical imaging device 100 to perform an exemplary type of surgical procedure, e.g., abdominal surgery. It should be recognized that this is merely one of many types of surgical procedures that may be performed with the surgical imaging device 100 of the present invention. According to this exemplary procedure and referring to FIG. 11(a), an incision 199 is made in the abdominal wall AW to the peritoneal fat layer PFL. The prongs 108a to 108d are inserted through the incision 199. In order to facilitate the insertion of the prongs 108a to 108d and to minimize the size of the incision required, the prongs 108a to 108d may be positioned by the user in the first position, e.g., the first position illustrated in FIG. 6 wherein the prongs 108a to 108d are parallel to each other. As the prongs 108a to 108d are inserted they separate the peritoneum P from the properitoneal fat layer PFL.

After the prongs 108a to 108d and the bottom portion 110 have been inserted into the incision, the user may use the control levers 112a to 112d to separate the prongs 108a to 108d. FIG. 11(b) illustrates the surgical imaging device 100 after the prongs 108a to 108d and the bottom portion 110 have been inserted into the incision and the prongs 108a to 108d have been separated. As shown in FIG. 11(b), the prongs 108a to 108d may be separated until the prongs 108a to 108d are in the second position, e.g., the second position illustrated in FIGS. 1 and 8 wherein the prongs 108a to 108d are approximately 90 degrees apart from each other relative to the central axis 104a of the body portion 104.

After the prongs 108a to 108d are separated the user may apply downward pressure to the retraction actuator 102. As the user extends retraction actuator 102 through the incision, the bottom portion 110 of the retraction actuator 102 pushes on the peritoneum P so that the peritoneum P is detached from the properitoneal fatty layer PFL, but without piercing the peritoneum P. In this manner, a cavity C is formed between the abdominal wall AW and the peritoneum P, allowing a surgeon with space to perform a surgical procedure. FIG. 11(c) illustrates the surgical imaging device 100 after the bottom portion 110 of the retraction actuator 102 has pushed the peritoneum P so as to form the cavity C between the abdominal wall AW and the peritoneum P. FIG. 11(c) also illustrates that during the extension of retraction actuator 102 and as the cavity C is formed between the abdominal wall AW and the peritoneum P, the prongs 108a to 108d are caused to bend in conformance with the curvature of the properitoneal fatty layer PFL. Once the prongs 108a to 108d are placed in the retracted position as shown in FIG. 11(c), the surgeon may provide power via power supply 210 to the light sources 115 and to the imaging sensors 118 so as to generate image data of the cavity C. In this retracted position, the image sensors 118 of each of the prongs 108a to 108d provide multi-directional views of the cavity C, allowing a surgeon to view the surgical procedure being performed in the cavity C from various angles. If additional views are required, the surgeon may manipulate the control levers 112a to 112d until the desired view is obtained.

Thus, the surgical imaging device of the present invention in accordance with various embodiments thereof, may reduce the difficulty in obtaining different views of a surgical site in a body cavity. Unlike conventional surgical cameras, which require a surgeon to remove the camera from a first incision, to make another incision in the patient, and to reinsert the camera into the second incision in order to change the view of the surgical site and/or to examine the surgical site from a different angle, the surgical imaging device of the present invention permits multiple views to be seen without removing the device. Instead, the surgeon may view the surgical site from different angles simply by viewing the image data from the various image sensors situated in different locations within the surgical site. Furthermore, if these views are inadequate, the surgeon may move the prongs 108a to 108d as desired via the control levers 112a to 112d to obtain new views without the need to remove the device or make additional surgical incisions.

Still further, the surgical imaging device of the present invention in accordance with various embodiments thereof provides for a single device that enables a cavity to be formed in the surgical site, thereby providing space for performing the surgical procedure. In addition, the surgical imaging device of the present invention in accordance with various embodiments thereof provides for one or more light sources that provide light in the surgical site, thereby enabling the image sensors to provide useful image data without the need for making additional incisions to insert additional light sources.

Several embodiments of the present invention are specifically illustrated and/or described herein. However, it will be appreciated that modifications and variations of the present invention are covered by the above teachings without departing from the spirit and intended scope of the present invention.

What is claimed is:

1. A surgical imaging device, comprising:
    a body portion defining a longitudinal axis extending therealong;
    at least one leg extending through the body portion, the at least one leg including a flexible prong disposed at a distal portion thereof;
    a camera positioned on the flexible prong of the at least one leg in a crosswise configuration, wherein the flexible prong is movable between a first condition in which a longitudinal axis of the flexible prong is substantially parallel to the longitudinal axis of the body portion and the camera is oriented to face a substantially perpendicular direction relative to the longitudinal axis of the body portion, and a second condition, in which the longitudinal axis of the flexible prong is substantially perpendicular to the longitudinal axis of the body portion and the camera is oriented to face a substantially distal direction;
    at least one control lever configured to actuate movement of the flexible prong in a plurality of transverse directions with respect to the longitudinal axis of the body portion; and
    at least one light guide extending through the at least one leg and the flexible prong.

2. The surgical imaging device of claim 1, further comprising at least one light source positioned adjacent the camera.

3. The surgical imaging device of claim 1, wherein the camera includes at least a lens and an imaging sensor.

4. The surgical imaging device of claim 1, wherein the camera is a charged coupled device (CCD).

5. The surgical imaging device of claim 1, wherein the camera is a complementary metal oxide semiconductor.

6. The surgical imaging device of claim 1, further comprising a data cable interconnecting the camera and an external processing source for transmitting image information from the camera to the external processing source.

7. The surgical imaging device of claim 1, wherein the camera is configured to wirelessly provide image information to an external processing source.

8. The surgical imaging device of claim 7, wherein the external processing source is a display unit for displaying the image information provided by the camera.

9. The surgical imaging device of claim 1, wherein the flexible prong is configured to bend from the first condition to the second condition, in the first condition the flexible prong is disposed within the body portion, and in the second condition the flexible prong is disposed distal of the body portion.

10. The surgical imaging device of claim 1, wherein the at least one flexible prong includes a control line having control leads and power leads, wherein the power leads are configured to transmit power to an imaging sensor of the camera and wherein the control leads are configured to control an intensity of light provided by a light source.

11. The surgical imaging device of claim 1, wherein the at least one leg is configured to rotatably move with respect to the longitudinal axis of the body portion upon an actuation of the at least one control lever.

12. The surgical imaging device of claim 1, further comprising a retraction actuator extending longitudinally through the body portion.

13. The surgical imaging device of claim 12, wherein the retraction actuator is configured to move axially relative to the body portion.

14. The surgical imaging device of claim 1, further comprising at least one memory device for storing data corresponding to operations and functions of the surgical imaging device.

15. The surgical imaging device of claim 14, wherein the data includes at least one of data related to camera movement, adjustment of light intensity, zoom magnification, color, brightness, or focus.

16. The surgical imaging device of claim 14, wherein the data includes at least one of model/serial number identification data, usage data, or image data.

17. The surgical imaging device of claim 16, wherein the model/serial number identification data identifies the surgical imaging device.

18. The surgical imaging device of claim 16, wherein the usage data is collected information related to hours of usage of the surgical imaging device and types of procedures viewed by the surgical imaging device.

19. The surgical imaging device of claim 16, wherein the image data includes at least one of still frames or video clips depicting body cavities.

20. The surgical imaging device of claim 16, wherein the image data are labeled and categorized while the surgical imaging device is in use.

21. The surgical imaging device of claim 1, wherein the surgical imaging device is selectively operated by a user in one of a wired configuration and a wireless configuration.

22. The surgical imaging device of claim 1, wherein the at least one light guide is a fiber optic light guide.

23. A method of utilizing a surgical imaging device during a surgical operation, the method comprising:
    providing a surgical imaging device including:
        a body portion defining a longitudinal axis extending therealong;
        at least one leg extendable through a lumen of the body portion, the at least one leg including a flexible prong disposed at a distal portion thereof;
        a camera positioned on the flexible prong of the at least one leg in a crosswise configuration; and
        at least one control lever configured to actuate movement of the flexible prong in a plurality of transverse directions with respect to the longitudinal axis of the body portion;
    inserting the flexible prong of the at least one leg through tissue and within a patient at the outset of the surgical operation while the camera is oriented to face in a substantially perpendicular direction relative to the longitudinal axis of the body portion;
    displacing a portion of the tissue thereby causing a cavity to be formed in the tissue at a location adjacent a distal end of the body portion;

bending the flexible prong relative to the longitudinal axis of the body portion thereby orienting the camera to face in a substantially distal direction;

actuating the at least one control lever to move the flexible prong in a plurality of transverse directions with respect to the longitudinal axis of the body portion; and inserting at least one light guide through the at least one leg and the flexible prong, the at least one light guide providing operable communication between the camera and at least one imaging sensor positioned on the body portion.

24. The method of claim 23, further comprising positioning at least one light source adjacent the camera.

25. The method of claim 23, further comprising providing the camera with at least a lens and an imaging sensor.

26. The method of claim 23, further comprising providing image information from the camera to an external processing source via a data cable.

27. The method of claim 23, further comprising wirelessly providing image information from the camera to an external processing source.

28. The method of claim 23, further comprising displaying image information provided by the camera via a display unit.

29. The method of claim 23, further comprising moving the flexible prong from an extended position disposed distal of the body portion to a retracted position disposed within the body portion.

30. The method of claim 23, further comprising rotatably moving the at least one leg with respect to the body portion upon actuation of the at least one control lever.

31. The method of claim 23, further comprising providing a retraction actuator within a lumen of the body portion and being extendable from a distal end of the body portion.

32. The method of claim 31, further comprising moving the retraction actuator axially relative to the body portion.

33. The method of claim 23, further comprising providing the surgical imaging device with at least one memory device for storing data corresponding to operations and functions of the surgical imaging device.

34. The method of claim 33, wherein the data includes at least one of data related to camera movement, adjustment of light intensity, zoom magnification, color, brightness, or focus.

35. The method of claim 33, wherein the data includes at least one of model/serial number identification data, usage data, or image data.

36. The method of claim 35, further comprising identifying the surgical imaging device via the model/serial number identification data.

37. The method of claim 35, further comprising manipulating the usage data pertaining to collected information related to hours of usage of the surgical imaging device and types of procedures viewed by the surgical imaging device.

38. The method of claim 35, further comprising viewing at least one of still frames or video clips of the image data depicting body cavities.

39. The method of claim 38, further comprising labeling and categorizing the image data while the surgical imaging device is in use.

40. The method of claim 23, further comprising selectively operating the surgical imaging device in one of a wired configuration or a wireless configuration.

41. The method of claim 23, wherein the at least one light guide is a fiber optic light guide.

* * * * *